United States Patent [19]

Blauth et al.

[11] Patent Number: 4,669,451

[45] Date of Patent: Jun. 2, 1987

[54] APPARATUS FOR POSTOPERATIVE AND OTHER EXERCISING OF ELBOW AND SHOULDER JOINTS

[75] Inventors: Walter Blauth, Kiel; Ernst Knoll, D-7800 Kiel, both of Fed. Rep. of Germany

[73] Assignee: Ernst Knoll, Umkirch, Fed. Rep. of Germany

[21] Appl. No.: 680,857

[22] Filed: Dec. 12, 1984

[30] Foreign Application Priority Data

Dec. 15, 1983 [DE] Fed. Rep. of Germany ....... 3345386

[51] Int. Cl.⁴ .............................................. A61F 5/01
[52] U.S. Cl. .................................... 128/25 R; 128/78
[58] Field of Search .................. 128/25 R, 25 B, 82.1, 128/83, 84 C, 85, 24 R, 24.2, 77, 78, 87 C, 88; 3/1.1, 1.2, 12, 12.1; 272/117

[56] References Cited

U.S. PATENT DOCUMENTS

| 1,257,297 | 2/1918 | Brown | 128/88 |
| 1,639,815 | 8/1927 | Siebrandt | 128/88 |
| 2,010,328 | 8/1935 | Siebrandt | 128/88 |
| 2,832,334 | 4/1958 | Whitelaw | 128/25 R |
| 3,089,700 | 5/1963 | Hotas | 272/117 |
| 3,683,897 | 8/1972 | Shield et al. | 128/25 R |
| 3,976,057 | 8/1976 | Barclay | 128/25 R |
| 4,149,532 | 4/1979 | Tarry et al. | 128/87 |
| 4,180,870 | 1/1980 | Radulovic et al. | 128/87 |
| 4,214,577 | 7/1980 | Hoy | 128/25 R |
| 4,487,199 | 12/1984 | Saringer | 128/25 R |

FOREIGN PATENT DOCUMENTS

| 2524468 | 12/1976 | Fed. Rep. of Germany | 128/25 R |
| 3030712 | 3/1982 | Fed. Rep. of Germany | 128/88 |
| 2535605 | 11/1982 | France | 128/25 R |
| 2542993 | 9/1984 | France | 128/77 |
| 119862 | 10/1947 | Sweden | 128/88 |

OTHER PUBLICATIONS

Sutter CPM 2000 S, Catalog 1984.

Primary Examiner—Richard J. Apley
Assistant Examiner—J. Welsh

[57] ABSTRACT

Apparatus for the exercising of an afflicted elbow and/or shoulder joint, especially for postoperative exercising of such joints, has a carriage which is placed adjacent to the back, chest or side of a patient's torso and is secured to the body of the patient by a strap or pad engaging the non-afflicted shoulder as well as by a lower component including one or more shells or a seat in the hip region. The arm support is attached to the carriage by two motion generating and transmitting units one of which is adjustably secured to the carriage and defines a horizontal pivot axis and the other of which is carried by one unit and defines a vertical pivot axis for the support. The two axes intersect each other in the afflicted shoulder joint. An additional motion generating and transmitting unit can be provided to pivot two articulately connected portions of the arm support in the region of the elbow. The controls for the units can be programmed so that the patient can perform exercises about one, two or more axes in a preselected sequence, to a predetermined extent and for predetermined intervals of time.

16 Claims, 10 Drawing Figures

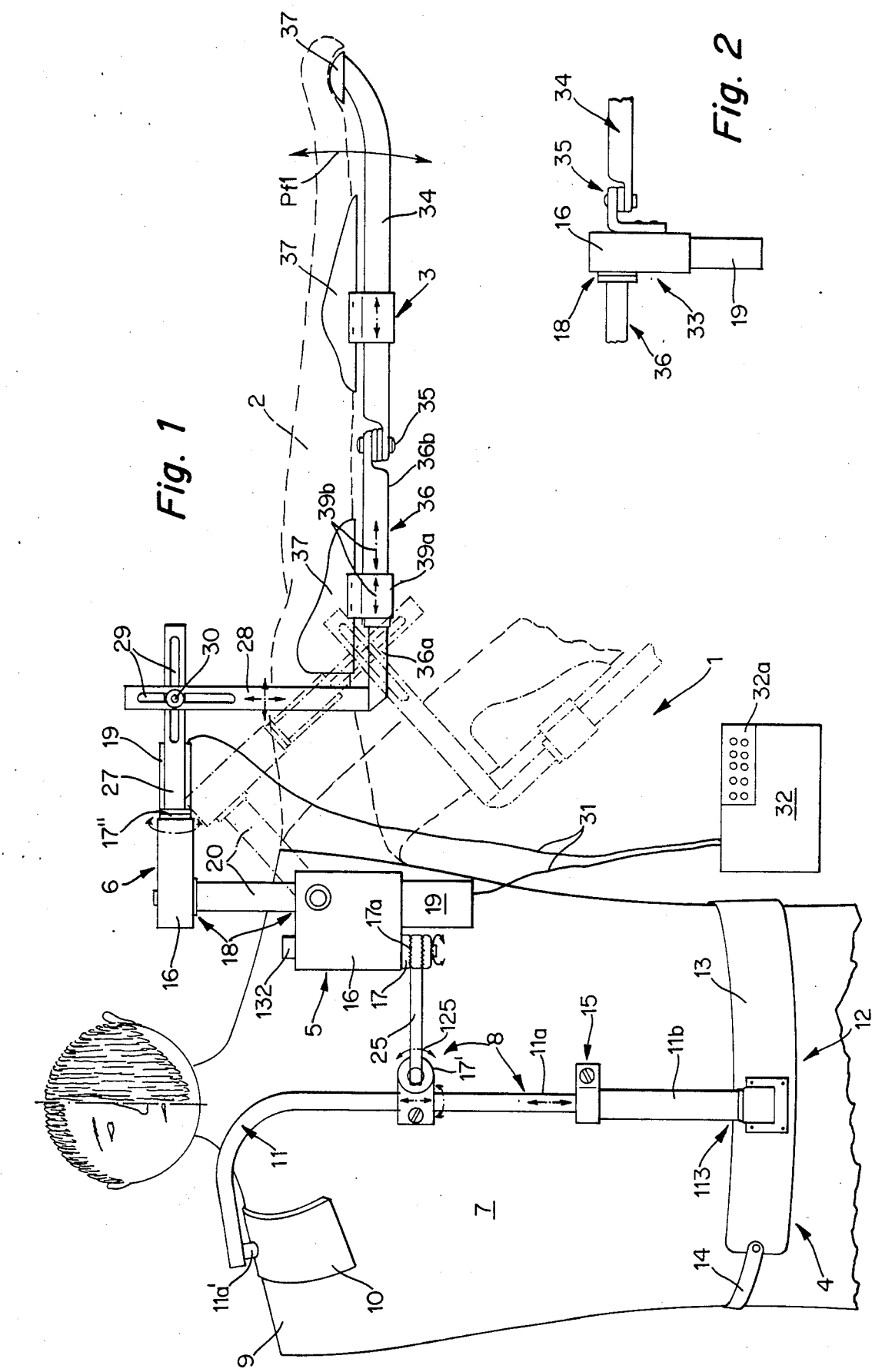

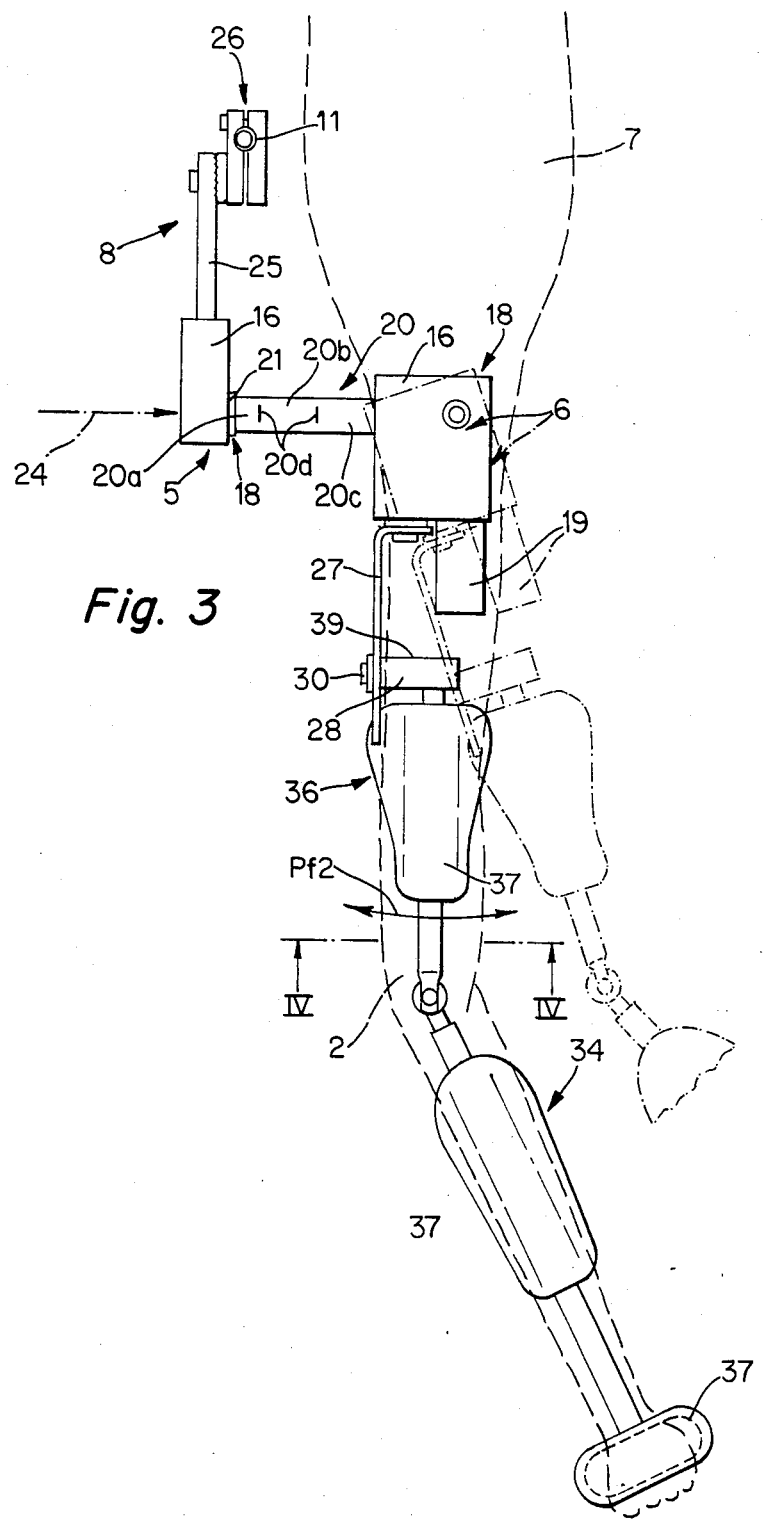

APPARATUS FOR POSTOPERATIVE AND OTHER EXERCISING OF ELBOW AND SHOULDER JOINTS

BACKGROUND OF THE INVENTION

The present invention relates to exercising apparatus in general, and more particularly to improvements in exercising apparatus for afflicted elbow and/or shoulder joints, especially for postoperative physical therapy such as that which is recommended following the implantation of shoulder end prostheses and/or osteosynthesis, contusions and/or tearing of muscles in the shoulder and/or elbow region, all kinds of illnesses involving the danger of stiffening of the shoulder joint, surgery in the region of the elbow, lower arm and/or upper arm, removal of calcereous deposits, as well as for the purpose of preventing contraction of muscles. The above are but a few examples of circumstances under which the exercising apparatus of the present invention can be put to use. Still more particularly, the invention relates to improvements in exercising apparatus of the type wherein one arm of the patient rests on a support which is affixed to a carriage and may but need not always be provided with a pivot in the region of an afflicted elbow joint so as to allow for flexure of the lower arm with reference to the upper arm.

It is already known to install an exercising apparatus for the shoulder and/or elbow of a patient on a chair or on a frame which can be placed next to the patient, e.g., next to a chair in which the patient is seated or next to a bed which is occupied by the patient. Such exercising apparatus exhibit a number of serious drawbacks, especially that they can be used by a patient only as long as the patient is sufficiently close to the chair, bed or frame carrying the exercising apparatus. Furthermore, and at least as important, it is not possible to invariably ensure that the apparatus will be held and will remain in an optimum position for use by a patient, for example, that the aforementioned support will be located in an optimum position with reference to the shoulder joint. Thus, while the various pivots of the apparatus may be adequately positioned relative to the afflicted elbow and/or shoulder joint prior to start of an exercise or a series of exercises, the positions of such pivot or pivots relative to the elbow and/or shoulder joint are highly likely to and normally do change with attendant problems such as pronounced discomfort as a result of articulation of the arm relative to the shoulder and/or of the lower arm with reference to the upper arm. Moreover, it is practically impossible to induce or force a patient to remain in a fixed position with reference to a stationary exercising apparatus for an extended period of time so that, at the very best, such conventional exercising apparatus can be used for relatively short intervals of time which might not be advantageous in connection with certain types of treatment. Still further, the weight, bulk and cost of conventional apparatus are considerable which is due, to a great extent, to the need for mounting such apparatus on a sturdy frame, on a sturdy chair or on a solid bed in order to ensure that the stationary parts of the apparatus will not change their positions while the apparatus is in actual use.

OBJECTS AND SUMMARY OF THE INVENTION

An object of the invention is to provide a novel and improved apparatus which is much more versatile than heretofore known apparatus for physical therapy of the arm and/or shoulder region of a patient.

Another object of the invention is to provide a lightweight, compact and relatively simple but rugged and reliable exercising apparatus which can be used with advantage by patients of all ages and both sexes, which can be rapidly adjusted to ensure convenient and painless utilization by a patient, and which allows for rapid, convenient and accurate positioning of its pivot or pivots in optimum location or locations with reference to the elbow and/or shoulder joint of the patient.

A further object of the invention is to provide a novel and improved method of exercising the afflicted elbow and/or shoulder joint of a patient.

An additional object of the invention is to provide an exercising apparatus which allows for a variety of relatively simple, more complex or highly complex exercises in any desired sequence or in randomly selected order, and which can be manipulated by a patient with a minimum of training and without any or with a minimum of supervision by physicians, nurses and/or other trained persons.

Still another object of the invention is to provide the apparatus with novel and improved means for supporting its pivot or pivots in an optimum position or in optimum positions with reference to one or more afflicted joints, especially an afflicted shoulder joint but also an afflicted elbow joint.

An additional object of the invention is to provide an apparatus which need not be permanently or even temporarily secured to a stationary frame or the like so that it greatly enhances the mobility of the patient who is in need of exercise.

Still another object of the invention is to provide the apparatus with novel and improved means for selecting the extent and/or the direction of movements which are to be performed by the arm and/or by the upper arm and/or by the lower arm of a patient.

A further object of the invention is to provide an exercising apparatus whose utilization is much less likely to be painful and/or tiresome to a patient than the utilization of heretofore known exercising apparatus.

An additional object of the invention is to provide the apparatus with novel and improved means for eliminating the need for installation in or on a stationary frame or the like.

Another object of the invention is to provide an exercising apparatus which is constructed and assembled in such a way that a patient can select the sequence and/or the extent of various exercises prior to as well as during actual use.

A further object of the invention is to provide a novel and improved apparatus for facilitating and carrying out movements of the arm of a patient with reference to the shoulder.

Another object of the invention is to provide novel and improved apparatus for exercising the elbow joint of a patient simultaneously with or independently of exercising the entire arm.

The invention resides in the provision of an apparatus for exercising an afflicted elbow and/or shoulder joint of a patient, particularly for postoperative exercising of such joint or joints. The apparatus comprises an elongated support (e.g., a suitably configured rail made of a lightweight metallic or synthetic plastic material) for that arm of the patient which is attached to the torso by the afflicted shoulder joint and/or which includes the afflicted elbow joint, a carriage for the support, means for separably affixing the carriage to the body of the patient, and means for articulately connecting the carriage with the support so as to define at least one pivot axis which intersects the afflicted shoulder joint of the patient wearing the apparatus. The support can include a first portion which is connected to the carriage by the connecting means, a second portion and means for pivotally coupling the first and second portions of the support to each other in the region of the elbow of the arm resting on the support. The connecting means can define a plurality of mutually inclined pivot axes which intersect each other in or close to the afflicted shoulder joint of the patient wearing the apparatus. The affixing means preferably includes means for securing the carriage to a shoulder of the patient wearing the apparatus, preferably to the shoulder which defines the other (normally non-afflicted) shoulder joint.

The connecting means preferably comprises first transmission means defining the one pivot axis, second transmission means defining a second pivot axis which intersects the one pivot axis in or close to the afflicted shoulder joint of the patient wearing the apparatus, and means for adjusting at least one of the transmission means relative to the other transmission means and hence also relative to the afflicted shoulder joint of the patient wearing the apparatus. Still further, the connecting means preferably comprises first means for pivoting the support about the one axis and second means for pivoting the support about the second axis. The one axis is preferably substantially horizontal (i.e., the support is pivotable about such axis in a substantially vertical plane) when the patient wearing the apparatus maintains her or his torso in a substantially upright position, and the second pivot axis is preferably vertical (i.e., the support can move about the second axis in a substantially horizontal plane) when the patient wearing the apparatus maintains her or his torso in the aforementioned (substantially upright) position.

The carriage can include a brace for one of the pivoting means and the transmission means which receives motion from the one pivoting means has an output element which preferably carries the other transmission means and the corresponding pivoting means.

The affixing means preferably includes a first component for securing the carriage to a shoulder of the patient and for thus positioning the connecting means with reference to the afflicted shoulder joint of the patient wearing the apparatus, and at least one additional component for securing the carriage to the body of the patient in the lower region of the torso so as to carry a substantial percentage of the overall weight of the apparatus when the latter is worn by the patient. The lower region of the torso may be the region of the hips and/or the region of the buttocks.

The transmission means which defines the vertical pivot axis can be located at a level above the afflicted shoulder joint of the patient when the patient wears the improved apparatus, and the transmission means which defines the horizontal pivot axis can be located at a level below the afflicted shoulder joint, either adjacent to the chest or adjacent to the back of the patient wearing the apparatus.

Each transmission means can comprise a self-locking transmission (e.g., a worm gear) having an input element which is driven by a prime mover (e.g., an electric motor) and an output element which transmits motion (directly or indirectly) to the support. The apparatus preferably further comprises control means for operating the prime mover means of the pivoting means e.g., a computerized control means which can operate the prime mover means in accordance with a predetermined program. Such apparatus can further comprise mechanical, optical and/or otherwise operated sensor means (e.g., one or more limit switches) for monitoring the extent and/or the direction of movement of the support and for transmitting to the control means signals denoting the extent and/or the direction of movement of the support about the one axis and/or about the second axis. Friction clutch means can be interposed between the support and at least one of the transmission means so as to permit for operation of the respective prime mover means while the support assumes at least one end position as considered in the direction of pivotal movement of the support about the one and/or the second axis. Such friction clutch means prevents excessive pivoting of the support and eventual injury or discomfort to the patient wearing the apparatus. The transmission means can be incorporated in (i.e., they can form part of) the respective pivoting means.

The first transmission means can include an arcuate bracket which overlies the afflicted shoulder of the patient wearing the apparatus, and the second transmission means can be affixed to one end portion of the bracket. The other end portion of the bracket is then arranged to pivot about the one axis and the second axis is preferably normal to the one axis, i.e., the two end portions of the bracket preferably make an angle of at least approximately 90 degrees. The second transmission means can be connected to the support by at least one link and the second pivoting means is then designed to pivot the link and the support about the second axis. The connection between the first transmission means and the carriage can include a holder, and such holder and the transmission means thereon are preferably adjustable with reference to each other about a further axis which is preferably normal to the one axis.

Means can be provided for pivoting the second portion of the support with reference to the first portion of such support, e.g., to exercise an afflicted elbow joint of the arm resting on the support.

The carriage can comprise an elongated substantially rod-like member having an arcuate upper section which overlies one shoulder of the patient wearing the apparatus. The affixing means of such apparatus can include a pad which serves to engage the one shoulder of the patient and is connected to the arcuate upper section of the rod-like member, e.g., by means of a fulcrum (such as a universal joint) which allows for changes in orientation of the pad with reference to the rod-like member.

A connector can be provided between the carriage and the affixing means so as to allow such parts to turn through substantially 180 degrees with reference to each other. This contributes to the versatility of the apparatus because the support can be used to serve as a rest for the right-hand arm or for the left-hand arm of a patient. The carriage can be assembled of several sections which are slidably telescoped into each other so that the carriage can be adjusted in order to conform the position of the affixing means to the body of the patient who is to wear the apparatus. The aforementioned holder of the carriage can be adjustably secured to the rod-shaped member of the carriage at one of its ends and can adjustably support the first transmission means at its other end. The carriage of such apparatus can include an elongated portion (such as the aforementioned rod-like member) which is substantially vertical when the patient wearing the apparatus maintains her or his torso in an at least substantially upright position, and the one end of the holder is then adjustable longitudinally of the elongated portion of the carriage. The first transmission means of such apparatus is preferably turnable with reference to the holder about an axis which is at least substantially parallel to the elongated portion of the carriage.

The carriage and the affixing means can constitute or form a corset which surrounds a part of the torso of the patient wearing the apparatus. The affixing means can comprise one or more shell-shaped components whose shape conforms to that of one or more selected portions of the torso of a patient wearing the apparatus. The affixing means can include means for maintaining the carriage adjacent to the chest or adjacent to the back of the patient. The carriage and the affixing means can constitute an arched unit whose curvature conforms, at least substantially, to the curvature of the chest or back of the patient. The affixing means can include a substantially shell-shaped component which surrounds a portion of the hip region of the torso of the patient wearing the apparatus and a flexible belt or strap which serves to releasably maintain the shell-shaped component in contact with the selected portion of the hip region. The affixing means can constitute or include some sort of a seat for the buttocks of the patient wearing the apparatus and a preferably elastically deformable coupling element which connects the seat to the carriage.

The connecting means can include means for adjusting the level of the first transmission means with reference to the carriage and the afflicted shoulder joint of the patient. Such adjusting means can include a rotary feed screw.

The novel features which are considered as characteristic of the invention are set forth in particular in the appended claims. The improved exercising apparatus itself, however, both as to its construction and its mode of operation, together with additional features and advantages thereof, will be best understood upon perusal of the following detailed description of certain specific embodiments with reference to the accompanying drawing.

BRIEF DESCRIPTION OF THE DRAWING

FIG. 1 is an elevational view of an apparatus which embodies one form of the invention and whose carriage can be placed adjacent to the chest or back of a patient, the torso of the patient being shown in upright position and the arm support being shown in a horizontal position;

FIG. 2 illustrates a portion of a modified support which can be used in the apparatus of FIG. 1 and is equipped with a motorized unit for exercising the elbow joint of the patient whose arm rests on the support;

FIG. 3 is a plan view of the support which is shown in FIG. 1 and further shows the means for connecting the support with the carriage;

DESCRIPTION OF THE PREFERRED EMBODIMENTS

Referring first to FIGS. 1 and 3 to 5, there is shown an apparatus 1 which can be used to exercise the arm 2 of a patient by moving the entire arm relative to an afflicted shoulder and/or to exercise the lower arm by moving it with reference to the upper arm. The arm 2 is shown in FIGS. 1 and 3 by broken lines. The apparatus 1 comprises an elongated support 3 (e.g, a composite rail or splint) which constitutes a rest for the arm 2. Such supports are often used to serve as rests for the arm following an operation in the region of the respective (afflicted) shoulder and also following an operation in the region of the (afflicted) elbow. The support 3 can be used as a stationary rest for the arm 2 but it can also be caused to transmit certain movements to the entire arm and/or to the lower arm, depending on the nature of the required physical therapy.

Figure 4:
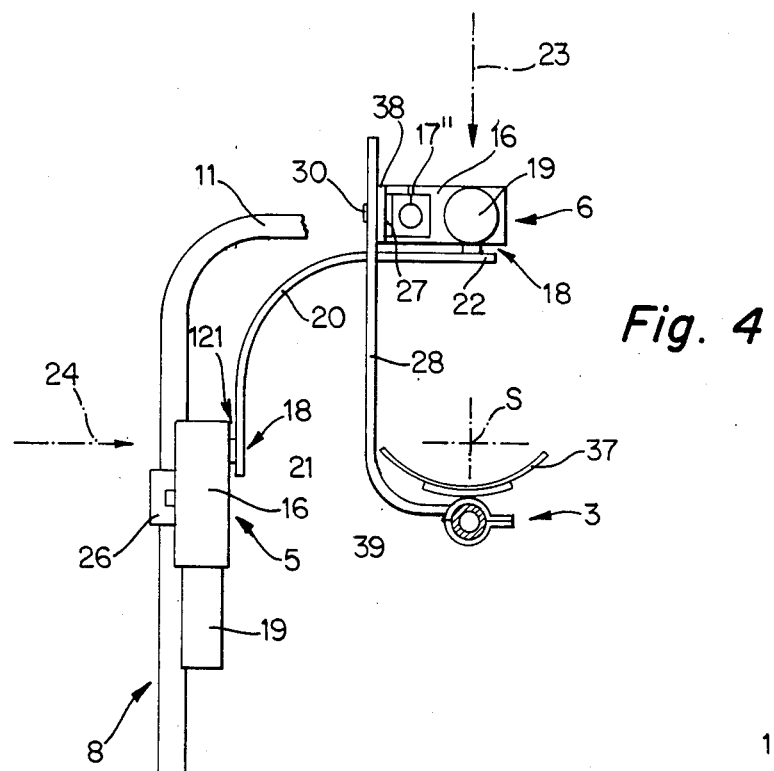
FIG. 4 is a vertical sectional view as seen in the direction of arrows from the line IV—IV of FIG. 3.

In addition to the support 3, the improved apparatus 1 comprises a second support 8 (hereinafter called carriage because it is designed as a mobile support for the arm support 3), a composite device for separably affixing the carriage 8 to the body (especially to the torso 7) of a patient, and means (including the units 5 and 6) for articulately connecting the support 3 with the carriage 8 in such a way that the support 3 can pivot about at least one axis (such as the axis 23 (shown in FIG. 3) or 24 shown in FIGS. 1, 3 and 4) which intersects the afflicted shoulder joint S (see FIG. 4) of the patient. The unit 5 defines the pivot axis 24 which is horizontal when the patient wearing the apparatus 1 maintains his or her torso 7 in a subsantially upright position (FIGS. 1 and 3). The unit 5 comprises a transmission which defines the axis 24 as well as a pivoting means or drive means which causes the support 3 to pivot about the axis 24, i.e., which causes the afflicted arm 2 to move in a vertical or nearly vertical plane in directions indicated by a double-headed arrow Pfl shown in the right-hand portion of FIG. 1. The unit 6 includes a transmission which defines the axis 23 and drive means for pivoting the support 3 about the axis 23. The latter is vertical when the torso 7 of the patient wearing the apparatus 1 assumes the aforementioned substantially upright position so that the unit 6 can cause the support 3 and hence the arm 2 to move in a substantially horizontal plane in directions which are indicated in FIG. 3 by a double-headed arrow Pf2. An intermediate position of the arm 2 is indicated by broken lines.

In the embodiment which is shown in FIGS. 1 and 3 to 5, the carriage 8 comprises an elongated tubular member 11 whose upper end portion is curved so as to overlie a part of the left-hand (non-afflicted shoulder 9 of the patient. The upper end portion of the member 11 carries a fulcrum 11a' (e.g., a universal joint) for a suitably arched shoulder pad 10 which can be coated with foam rubber or the like and comes to rest on the non-afflicted shoulder 9 so as to stabilize the connecting means including the units 5 and 6 with reference to the afflicted shoulder joint when the carriage 8 is properly affixed to the torso 7. The shoulder pad 10 can be said to form part (the upper component) of the affixing device 4. The lower oomponent of the affixing device 4 is attached to the lower end portion of the rod-like member 11 of the carriage 8 by a relatively wide band-like shell 13 which surrounds the major part of the hip region 12 of the torso 7 and a flexible belt or strap 14 which surrounds the remaining portion of the torso 7 in the hip region 12 and ensures that the shell 13 is held in proper position for retention of the pivot axes 23 and 24 in optimum locations with reference to the afflicted shoulder joint S. The universal joint (fulcrum 11a) can be replaced with a simpler fulcrum (e.g., one which defines only one pivot axis or only two pivot axes for the shoulder pad 10 (upper component) of the affixing device 4). The shell 13 can surround at least one half but also up to and even in excess of three fourths of the torso 7 in the hip region 12, especially if it is elastically deformable, otherwise deformable or contains a hinge at its middle (i.e., opposite the strap 14). It has been found that the illustrated lower component 13, 14 of the affixing device 4 ensures a surprisingly stable mounting of the units 5, 6 and hence of the support 3 on the torso 7 of the patient who is required to wear the apparatus 1. Moreover, the affixing device 4 is capable of adequately transmitting tilting and/or other stresses in part to the non-afflicted shoulder 9 and in part to the hip region 12 of the torso 7. The major part of the overall weight of the apparatus 1 is taken up by the hips of the patient.

Figure 5:
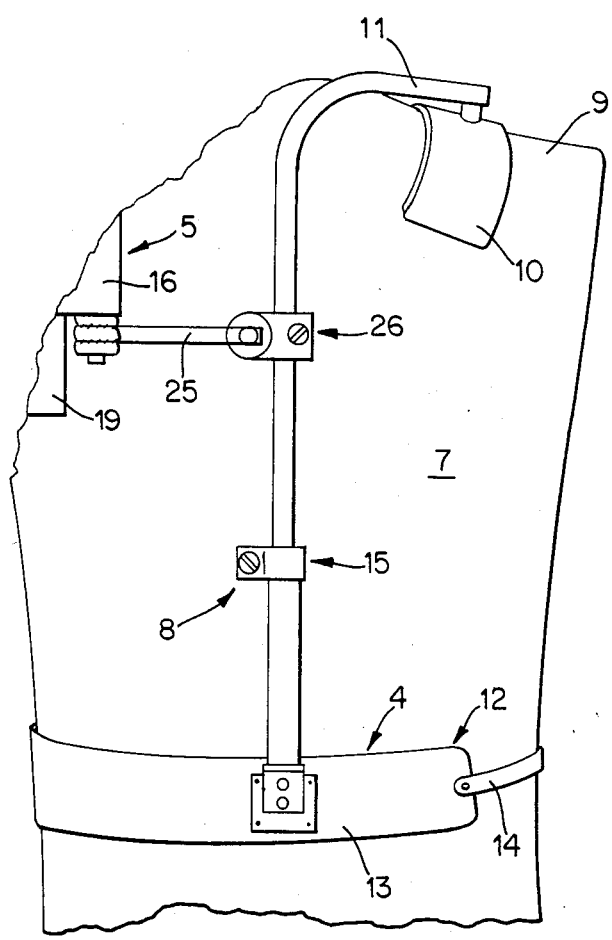
FIG. 5 shows a portion of the apparatus of FIG. 1 in inverted position in which it can exercise he left-hand shoulder joint.

As can be readily seen in FIGS. 1 and 5, the shell 13 of the lower component of the affixing device 4 surrounds the hip region 12 at that side of the torso 7 which is located below the afflicted shoulder. This is advisable and advantageous because the shell 13 can take up the major part of forces which are developing (a) as a result of the mass or weight of the apparatus 1 and (b) in the zone below the units 5 and 6 so as to even more reliably ensure that the weight of the apparatus 1 need not be taken up by the afflicted shoulder. At the present time, it is preferred to design the lower component of the affixing device 4 in such a way that the strap 14 serves, either exclusively or predominantly, as a means for maintaining the shell 13 in an optimum position to take up the weight of the apparatus and other forces. The one and/or the other end portion of the strap 14 can be secured to the corresponding end portion of the shell 13 by snap fasteners or the like in order to allow for rapid attachment of the apparatus to or for rapid detachment from the torso 7. The length of the strap 14 is or can be adjustable so as to ensure that the inner side of the shell 13 overlies and conforms rather snugly to the shape of the respective portion of the hip region 12.

Figure 6:
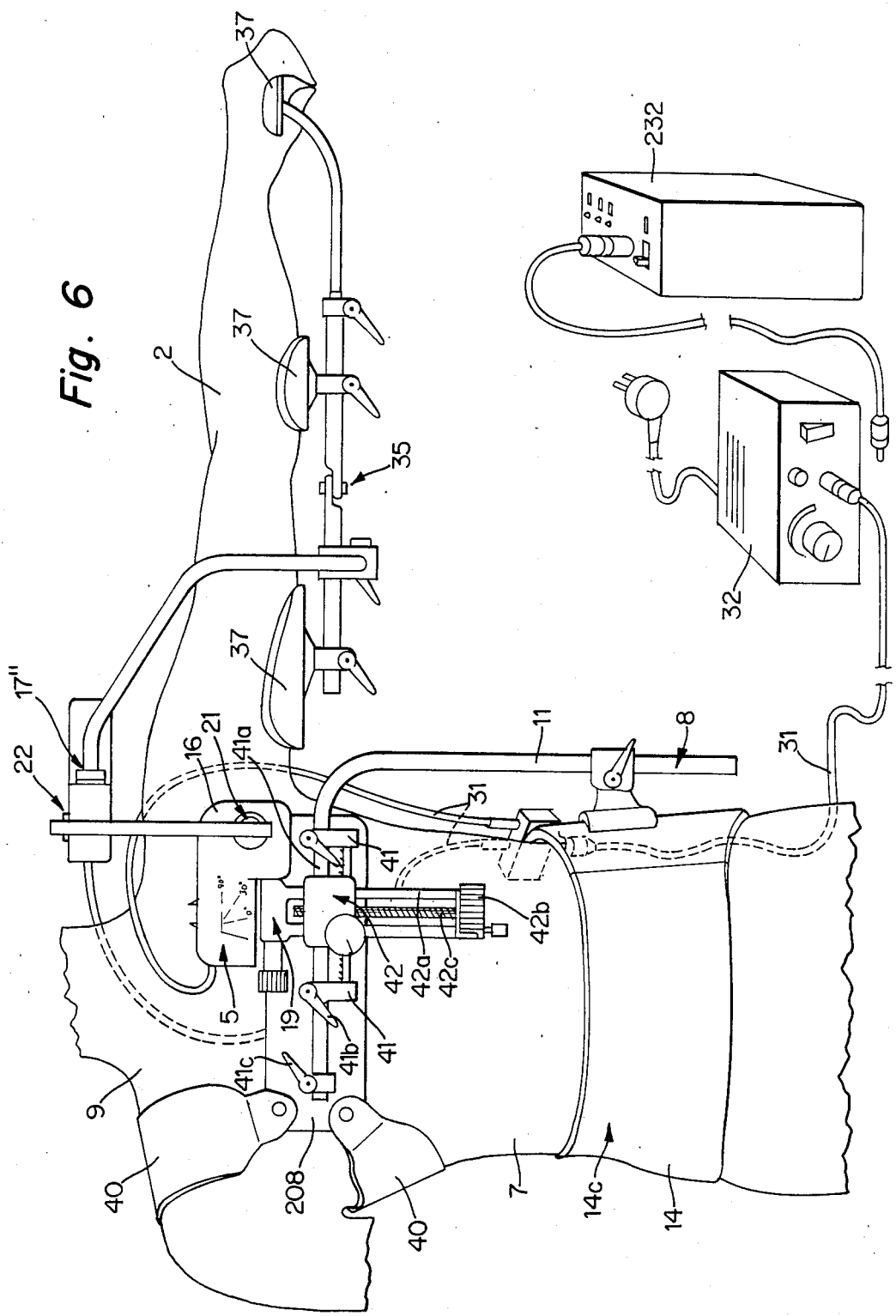
FIG. 6 is an elevational view of a modified apparatus with a different affixing device, a different carriage and different connecting means between the carriage and the arm support, a portion of the carriage being adjacent to the chest of the patient.
Figure 7:
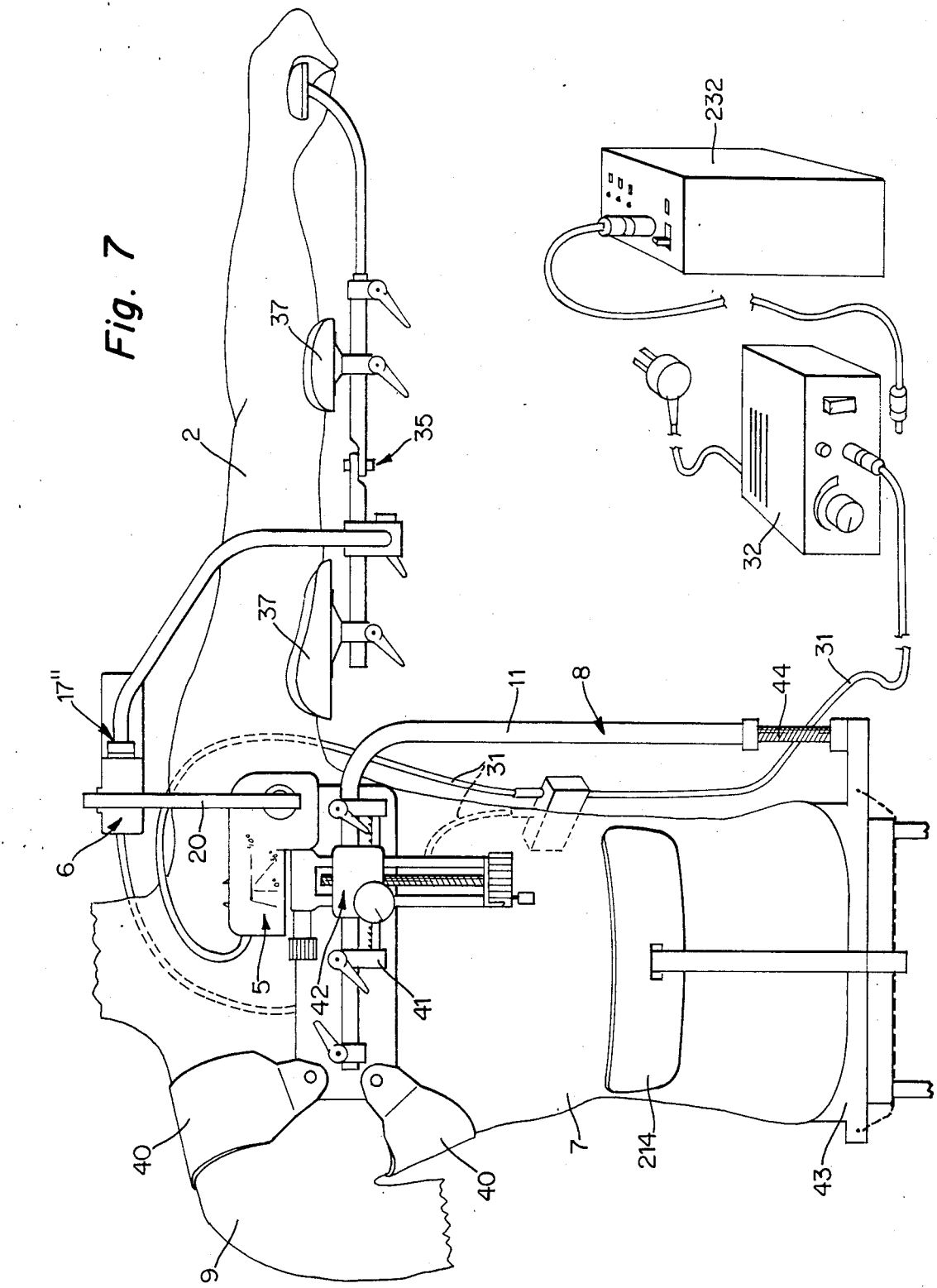
FIG. 7 illustrates a further apparatus which constitutes a modification of the apparatus of FIG. 6 and wherein the affixing device comprises a seat for the patient.

The elongated tubular or rod-like member 11 of the carriage 8 preferably consists of several sections (such as those denoted by the numerals 11a and 11b) which are slidably telescoped into each other and can be held in selected positions by a suitable clamping device 15. This renders it possible to conform the distance between the shoulder pad 10 and the shell 13 of the affixing device 4 to the height and bulk of the torso 7. As can be seen in FIGS. 6 and 7, the arcuate shoulder pad 10 can be replaced with a relatively wide shoulder strap 40 which surrounds the major part of the non-afflicted shoulder 9 and extends below the arm pit to even more reliably stabilize the positions of the units 5 and 6 with reference to the afflicted shoulder joint.

The unit 5 of the means for connecting the carriage 8 with the arm support 3 comprises a housing 16 which is connected to a substantially horizontal holder 25 of the carriage 8 by a coupling 17 defining a pivot axis which is parallel to the straight (upright) major part of the rod-like member 11 of the carriage 8. The coupling 17 comprises a detent structure in the form of cooperating annuli of teeth indicated at 17a which can releasably hold the unit 5 (i.e., the housing 16 of the unit 5) in a selected angular position with reference to the corresponding end portion of the holder 25.

The other end portion of the holder 25 is provided with a similar coupling 17' which enables the holder to pivot in the directions indicated by a double-headed arrow 125. The coupling 17' also comprises a detent structure which corresponds to the detent structure 17a but cannot be seen in FIG. 1. This coupling is mounted on a clamp 26 which is releasably secured to the upright portion of the rod-like member 11 of the carriage 8 so that it can be shifted up or down (nearer to or further away from the shell 13) and fixed in an optimum position for the patient wearing the apparatus 1. It will be seen that the holder 25, the two couplings 17, 17' and the clamp 26 allow for a practically unlimited adjustability of the unit 5 with reference to the member 11 within limits which are imposed by the desired overall weight of the apparatus 1 and the anticipated need for adjustability in order to enable one and the same apparatus to be properly mounted on the torso 7 of a short or tall, stout or skinny, youthful or adult patient.

Figure 10:
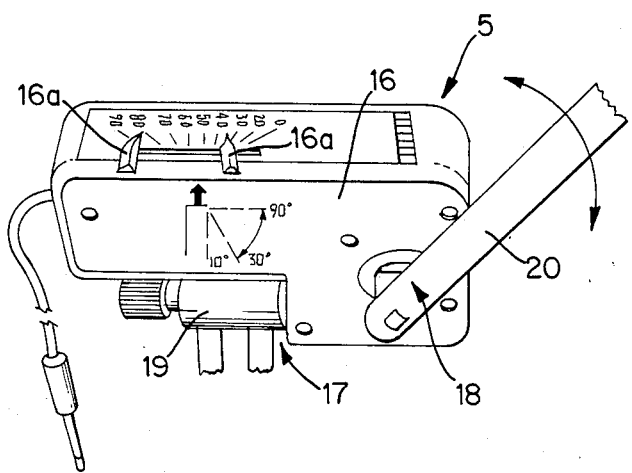
FIG. 10 is a perspective view of one of the motorized pivoting means in the apparatus of the present invention.

The housing 16 of the unit 5 contains the transmission 18 which has an output element 20 turnable about the axis 24 in order to move the support 3 through the medium of the unit 6. The transmission 18 further includes an input element which is the output element of a prime mover 19 here shown as a reversible electric stepping motor serving to pivot the output element 20 in stepwise fashion and in a clockwise or counterclockwise direction as viewed in FIG. 1. The transmission in the housing 16 of the unit 5 can constitute a conventional worm gear which is a self-locking structure so that the output element 20 invariably remains in a selected angular position (with reference to the axis 24) for any desired interval of time by the simple expedient of arresting the motor 19. The worm wheel of the transmission 18 can pivot the output element 20 and can receive torque from a worm which is driven by the prime mover 19. The means for selecting the extent of angular movement of the output element 20 about the axis 24 can be constructed in a manner as shown in FIG. 10, i.e., the housing 16 of the unit 5 can carry a suitably graduated scale with shiftable selectors 16a which reverse the direction of angular movement of the output element 20 after the element 20 has completed a turn through a desired angle, e.g., an angle of between 10 and 90 degrees with reference to a vertical plane. A diagrammatic drawing can be applied to the housing 16 of the unit 5 next to the scale in order to assist the operator (e.g., the patient) in properly locating the selectors 16a with referance to the housing 16.

The illustrated output element 20 is a arcuate bracket the upper end portion 22 of which overlies the afflicted shoulder of the patient wearing the apparatus 1 and extends at an angle of 90 degrees with reference to its lower end portion 21 which can turn about the axis 24 in response to activation of the motor 19. The upper end portion 22 of the output element 20 carries the second unit 6 whose construction is preferably analogous to or identical with that of the unit 5. Thus. the unit 6 also comprises a housing 16 for a worm gear or another suitable self-locking transmission 18 and a reversible electric motor 19 (FIG. 3). The output element of the worm gear transmission 18 in the housing 16 of the unit 6 is adjustably connected with an enlongated link 27 by a coupling 17″ which can be identical with or analogous to the coupling 17 or 17′. The coupling 17″ enables the link 27 to turn with reference to the housing 16 of the unit 6 about an axis which is horizontal as viewed in FIG. 1 and vertical as viewed in FIG. 3. It will be noted that, since the unit 6 is mounted on the upper end portion 22 of the output element 20 of the transmission 18 in the housing 16 of the unit 5, the entire unit 6 (and hence the support 3) is compelled to share the angular movements of the output element 20 about the axis 24. The motor 19 of the unit 5 can be operated independently of or simultaneously with the motor 19 of the unit 6, or vice versa. This enhances the versatility of the apparatus 1 and enables the patient to perform a wide variety of exercises within the entire anatomically desirable or permissible range. FIG. 1 shows (by phantom lines) one of the practically infinite number of different positions of the support 3 with reference to the horizontal pivot axis 24, and FIG. 3 shows (again by phantom lines) one of the practically infinite number of positions of the support 3 with reference to the vertical axis 23.

FIG. 3 shows that the axes 23 and 24 intersect each other in or very close to the shoulder joint S. Such situation develops after a rather simple adjustment of the positions of units 5 and 6 with reference to the carriage 8 and affixing device 4 (and hence with reference to the torso 7 of the patient wearing the apparatus 1). The positions of the units 5 and 6 with reference to the shoulder joint S can be adjusted by releasing the clamping device 15 (so as to allow for an increase or reduction of the overall length of the member 11), by releasing the clamp 26 (so that the holder 25 can be shifted longitudinally of the member 11), by changing the position of the holder 25 with reference to the axis which is defined by the coupling 17′, by changing the position of the housing 16 or the unit 5 with reference to the axis defined by the coupling 17, by changing the position of the link 27 with reference to the axis which is defined by the coupling 17″, and/or by changing the inclination or the support 3 with reference to the link 27. The axes of the couplings 17, 17′ make an angle of 90 degrees. The just described numerous possibilities of adjustment of the positions of units 5 and 6 with reference to the shoulder joint S render it possible to cause the axes 23 and 24 to intersect each other in the joint S regardless of whether the apparatus 1 is borne by a short or tall, chunky or slim, muscular or flabby, rawboned or delicate patient.

The link 27 is adjustably connected with a second link 28 which directly carries the adjacent end portion of the support 3. As can be seen in FIG. 1, the links 27, 28 are provided with elongated closed slots 29 which intesect each other and receive the shank of a fastening device 30 which can maintain the link 28 (and hence the arm 2 on the support 3) in a selected angular position with reference to the link 27. The fastening device 30 can comprise a bolt and a nut. The reference character 38 indicates a prop which can be provided on or affixed to the link 27 to assist the fastening device 30 in maintaining the link 28 in a selected angular position with reference to the link 27. The link 27 is substantially horizontal when the support 3 is substantially horizontal, and the link 28 is then vertical or nearly vertical. The lower end portion of the link 28 has a laterally extending projection or extension 39 which makes an angle of 90 degrees with the longitudinal direction of the slot 29 in the link 28 and is preferably adjustably secured to the adjacent end portion of the support 3 by a clamping sleeve 39a or the like (note FIG. 1 and the double-headed arrows 39b therein). The extension 39 extends to a level below the adjacent end portion of the support 3 when the latter is held in the horizontal position of FIG. 1.

The adjustability of the link 28 relative to the link 27 renders it possible to conform the apparatus 1 to the length of the arm 2 of a patient, to the thickness of the arm as well as to the selected location where the inner end portion of the support 3 engages the arm 2, either directly or through the medium of a cushion 37 containing or consisting of foam rubber or the like.

The output element 20 can be assembled of several sections 20a, 20b, 20c which are slidably telescoped into each other and can be held in selected positions by suitable clamping devices 20d. This renders it possible to adjust the position of the unit 6 relative to the unit 5, i.e., to adjust the position of the axis 23 with reference to the axis 24 and shoulder joint S.

FIG. 1 shows that the motors 19 of the units 5 and 6 are connected to a control unit 32 by cables 31. The control unit 32 can be programmed to ensure that the movements of the support 3 about the axis 23 and/or 24 will take place in a predetermined sequence and to a predetermined extent. The panel 32a of the control unit 32 can comprise a number of pushbuttons or other actuating elements which can be depressed and/or otherwise moved in order to select the desired sequence of movements. Such selection can be made by a physician, by a nurse or by the patient. For example, the sequence of movements can be programmed by the physician or by the nurse, and the movements can be initiated by the patient when the need for the exercise arises. This greatly reduces the overall cost of physical therapy because a skilled person need not be present at the time of exercising but only to select an optimum program for the sequence of movements which are to be performed about the axis 23 and/or 24. Thus, a physical therapist in a hospital specializing in the treatment of certain diseases and/or specializing in surgery pertaining to the treatment of shoulder and/or elbow joints can take care of a large number of patients by simply selecting the desired sequence of movements and inspecting, when the need arises, the influence of selected exercises upon the patients. Moreover, it is possible to send a patient home within days after an operation and to program the control unit 32 so that the patient can perform her or his exercises at the required intervals at her or his home rather than in a hospital. This can greatly reduce the cost of surgery and/or other treatment by reducing the overall time which a patient must spend in the hospital or under direct supervision of a physician or nurse.

The motors 19 can constitute conventional stepping motors which can move the support 3 at a desired speed and to a desired extent with a high degree of accuracy and reproducibility. Limit switches (one shown at 132 in FIG. 1 to respond to a predetermined angular displacement of the output element 20 in a counterclockwise direction) can be provided to transmit to the control unit 32 appropriate signals denoting the direction and/or the extent of angular displacement of the support 3 about the axis 23 and/or 24. The limit switches can be replaced by or used jointly with other types of sensors and monitoring means which are connected in circuit with the control unit 32 and ensure that the support 3 will perform movements in directions and to the extent best suited for a particular treatment, e.g., immediately or shortly after an operation. Pressure-responsive switches, optoelectronic switches and/or other types of monitoring means can be used, depending on the desired degree of sophistication of the control unit 32 and/or on the desired extent of programming of the sequence of movements to be performed by the support 3 and the arm 2 thereon. The control unit 32 can be provided in addition to or in lieu of the controls which are shown in FIG. 10.

It is often further advisable to provide friction clutches or analogous means in order to ensure that the extent of angular movement of the support 3 about the axis 23 and/or 24 will not exceed a certain value which could result in injury or unnecessary discomfort to the patient. For example, FIG. 4 shows a friction clutch 121 which is installed between the end portion 21 of the output element 20 and other parts of the worm gear transmission 18 in the housing 16 of the unit 5 and serves to ensure that the motor 19 can continue to drive the movable parts of the worm gear in the housing 16 of the unit 5 when the support 3 reaches a preselected end position during movement about the axis 24. A similar friction clutch can be installed in the power train between the unit 6 and the support 3 to prevent excessive angular movements of the support about the axis 23. The friction clutch or clutches 121 can be used in addition to or in lieu of the aforediscussed limit switches and other monitoring means.

An advantage of units 5 and 6 which embody worm gears or other suitable self-locking transmissions 18 is that the support 3 automatically remains in a selected angular position in response to stoppage of the corresponding motor 19. Thus, by operating the motors 19 for a certain interval of time and/or at a preselected speed so as to move the support 3 to a predetermined angular position, the support 3 can perform the function of any conventional prop or splint for an injured arm or shoulder by maintaining (as long as necessary) the arm 2 in a selected position with reference to the torso 7 of the patient wearing the apparatus 1. There is no absolute need for specially designed locking and arresting means which would hold the support 3 in a selected position because the self-locking transmissions 18 in the housings 16 of the units 5 and 6 ensure automatic and reliable retention of the support 3 in a selected position as soon as the respective motors 19 are brought to a halt. The provision of self-locking transmissions in the housings 16 of the units 5 and 6 is advisable and desirable on the additional ground that, if the control unit 32 and/or its energy source 232 (see FIGS. 6 and 7) fails, the support 3 does not immediately leave its position under the action of gravity and/or under the weight of the arm 2 thereon but simply remains in the position in which it was held at the time of power failure. The control unit 32 can be equipped with its own energy source (i.e., the energy source 232 can constitute a battery or a set of batteries) or it can be connected with a normal outlet by a relatively long or short cord.

FIG. 1 further shows that the portion 36 of the support 3 is assembled of several sections 36a, 36b which are slidably telescoped into each other and can be held in selected positions by the aforementioned clamping sleeve 39a or by a discrete clamping device. It is clear that the other portion 34 of the support 3 can also comprise (or that only the portion 34 can comprise) two or more sections which are slidably telescoped into each other so as to allow for additional adjustments and to thus ensure greater comfort to the arm 2 resting on such adjustable support. Each of the portions 34, 36 carries one or more cushions 37 which come into direct contact with the adjacent portions of the arm 2 and can be lined with foam rubber or other relatively soft material in order to render the wearing of the apparatus 1 more comfortable to a patient.

The lower end portion of the rod-like member 11 of the carriage 8 is coupled to the shell 13 by a connector 113 which enables the shell 13 to turn through 180 degrees so as to be ready for the application to the other part of the hip region 12 (namely to that part of the hip region 12 which is bounded in part by the strap 14 of FIG. 1). This enhances the versatility of the apparatus 1 because it can be mounted in an optimum position for supporting the illustrated arm 2 or the other arm of the patient whose torso 7 is shown in FIG. 1. All that is necessary is to pivot the shell 13 in the just discussed manner at 113 and to change the orientation of the pad 10 by temporarily loosening the clamping device 15 which then permits the upper section 11a of the member 11 to turn about the axis of the lower section 11b of such member.

It is further within the purview of the invention to replace the affixing device 4 and/or the affixing device plus the carriage 8 with a corset (see FIG. 6) which is applied around a selected portion of the torso. It is equally possible to replace the single shell 13 and the strap 14 of FIG. 1 with a modified lower component of the affixing device 4, e.g., with a component having two or more interconnected but mutually adjustable shells or pads which can hug a selected portion of the torso with a sufficient force to ensure that the positions of the axes 23, 24 with reference to the shoulder joint S of the patient wearing the apparatus will remain at least substantially unchanged when such modified affixing device is properly applied. For example, the lower component of the affixing device can comprise two mirror symmetrical shells and suitable means for releasably and/or adjustably securing such shells to each other so as to allow for their application to or for their detachment from selected portions of the torso.

FIG. 1 shows the head of the patient partly from the rear and partly from the front side. This is intended to indicate the pronounced versatility of the improved apparatus, i.e., that the apparatus can be mounted in such a way that the carriage 8 is adjacent to the chest or to the back of the wearer. The decision to mount the apparatus in such a way that the carriage 8 is adjacent to the chest or to the back of a patient will depend on a number of parameters. For example, the carriage 8 will be adjacent to the back if the patient is to perform certain arm movements in a forward direction, i.e., about the axis 23 which is defined by the unit 6; the placing of the carriage 8 next to the back of the patient allows for a wider range of such forward movements because the carriage 8 is next to the back of the patient allows for a wider range of such forward movements because the carriage 8 is not in the way. On the other hand, it is desirable to place the carriage 8 next to the chest if the patient is to be seated and must or should or would like to place her on his back into contact with the customary back rest of a chair, sofa or another piece of furniture. Moreover, a patient can more readily reach a number of adjustable parts if the carriage 8 is adjacent to the chest so that the patient can readily adjust the optimum normal or starting position of the support 3 in which the arm 2 rests comfortably on the cushions 37. The patient can actually look at a substantial number of adjustable parts if the carriage 8 is adjacent to her or his chest. For example, the patient is likely to carry out some adjustments after sitting down on a chair or the like because seating entails a shortening of the distance between the shoulders and the hip region 12 so that the apparatus might not be comfortable without any adjustments after the patient has decided to sit down. The placing of the carriage 8 in front of the chest greatly simplifies and facilitates the necessary adjustments, e.g., by the patient so that the patient need not be continuously attended to by a nurse or another person during each and every stage of her or his recovery. Shortening of the distance between the shoulders and the hip region 12 as a result of sitting down can be compensated for by allowing or causing the upper section 11a of the member 11 of the cariage 8 to penetrate deeper into the lower section 11b.

Another reason for the placing of the carriage 8 next to the chest of a patient is that the patient (e.g., an elderly person) may have a pronouncedly curved or arched back so that it would be difficult or plain impossible to properly apply a standard apparatus to her or his torso. Of course, it is equally within the purview of the invention to furnish the improved apparatus with one or more spare members 11 each of which has a different shape (particularly a different curvature) so as to allow for rapid conversion of the carriage 8 into one which can be placed adjacent to the back of a patient whose back exhibits a pronounced or even very pronounced curvature (e.g., a hump). The same applies for the application of the carriage 8 next to the chest of a patient, i.e., the apparatus can be furnished with one or more spare members 11 so as to ensure that one of the total number of such members will best conform to the undulations of the chest.

Still further, it is within the purview of the invention to use an asymmetrical carriage. For example, the carriage 8 of FIG. 1 can be located to the right or to the left of the position which is shown in FIG. 1 if this is more convenient or comfortable to a patient or is more satisfactory in connection with the physical therapy following a certain operation or a certain illness. Reference may be had, for example, to FIG. 6 which shows that the elongated rod-like member 11 of the carriage 8 is adjacent to one side of the torso 7. The member 11 is located below the arm pit of the afflicted arm 2 and the upper component of the affixing device includes the aforementioned shoulder strap 40 which surrounds the major part of the unafflicted shoulder 9. The carriage 8 of FIG. 6 further includes a plate-like part 208 which supports the unit 5. The latter is adjacent to the chest or to the back of the patient, i.e., it is located at a level below the afflicted shoulder joint. The unit 6 is located at a level above the afflicted shoulder joint. The lower component of the affixing means shown in FIG. 6 includes a relatively short corset 14c which is preferably elastic and surrounds the entire hip region or the major part of the hip region. The apparatus of FIG. 6 is especially reliable as regards the retention of pivot axes defined by the units 5 and 6 in optimum positions with reference to the afflicted shoulder joint.

The corset or lower component of the affixing device which is shown in FIG. 6 can include a more or less rigid (or less elastic) portion or shell 13 and an elastic portion 14 which is separably or permanently affixed to the shell 13.

The aforementioned plate-like part 208 of the carriage 8 which is shown in FIG. 6 supports means for effecting a highly accurate adjustment of the support 3 in a horizontal as well as in a vertical direction. The adjusting means includes a horizontally movable follower 41 which is slidable along an elongated horizontal guide 41a (this guide can constitute the upper section of the member 11) and can be fixed in a selected position by locking devices 41b. The guide 41a can be moved relative to the part 208 and can be fixed in a selected position by one or more locking devices 41c. The follower 41 is shiftable along the guide 41a with the housing of a transmission 42 which can shift a vertically movable carrier 42a for the unit 5. The carrier 42a can be moved up and down by a motor 42b through the medium of a feed screw 42c. Thus, the unit 5 can be moved toward and away from the non-afflicted shoulder 9 by causing the follower 41 to slide along the guide 41a, and the unit 5 can be moved up or down by starting the motor 42b so as to rotate the feed screw 42c in a clockwise or in a counterclockwise direction. The provision of a feed screw 42c is desirable and advantageous because it is self-locking and also because it allows for highly accurate adjustments of the level of the unit 5. The unit 6 shares all movements of the unit 5 in response to shifting of the follower 41 along the guide 41a and/or in response to movement of the carrier 42a as a result of starting of the motor 42b.

FIG. 7 shows a further apparatus which constitutes a modification of the apparatus of FIG. 6. One of the differences between the apparatus of FIGS. 6 and 7 is that the latter apparatus comprises a seat 43 for the buttocks of the patient, a back rest 214 which contacts the torso 7 of the patient at the general level of the hips, and a shoulder strap 40 which is identical with or similar to the similarly referenced strap of FIG. 6. The member 11 of the carriage 8 is connected with the seat 43 by an elastomeric coupling element 44 which allows for a certain extent of movement of the torso 7 with reference to the seat 43. The structure of FIG. 7 allows for convenient treatment of a seated patient. When the patient is seated, the major part of the weight of the apparatus is borne by the seat 43. When the patient rises, the major part of the weight is carried by the strap 40.

An important advantage of the shoulder pad 10 and of the shoulder straps 40 is that the non-afflicted shoulder 9 can take up stresses which, in the absence of the part 10 or 40, would have to be borne at least in part by the afflicted shoulder. This renders it possible to exercise the afflicted shoulder soon after surgery or another type of treatment. However, it is also possible to design the apparatus in such a way that the pad 10 rests on (or that the strap 40 surrounds) the afflicted shoulder. This may be advisable in connection with certain postoperative exercises which should involve moderate or slight stressing of the afflicted shoulder.

Figure 9:
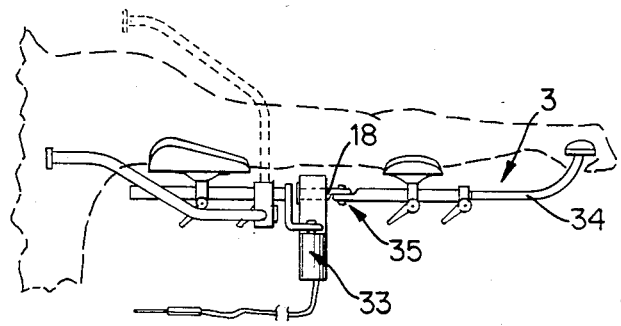
FIG. 9 illustrates a modification of the supports which are shown in FIGS. 2 and 8.

FIGS. 2 and 9 show a portion of a modified apparatus wherein a further unit 33 is provided to pivot the portion 34 of the support 3 with reference to the portion 36 about an axis which is defined by a coupling 35. The unit 33 also comprises a housing 16 and a motor 19 which drives a worm gear 18 or another suitable (preferably self-locking) transmission in the interior of the housing 16. When the support including the portions 34 and 36 of FIG. 2 is horizontal or nearly horizontal and the torso of the patient wearing such apparatus is upright or nearly upright, the axis which is defined by the coupling 35 is vertical or nearly vertical so that the lower arm of the patient can pivot in a substantially horizontal plane. The axis which is defined by the coupling 35 intersects the elbow joint of the arm 2 on the support including the portions 34, 36 of FIG. 2. In the embodiment which is shown in FIG. 2, the unit 33 is mounted in such a way that its housing 16 is connected with the coupling 35 and the transmission 18 therein transmits motion to the portion 36 of the support. In the embodiment of FIG. 9, the drive 18 is connected with the portion 34 by way of the coupling 35.

Figure 8:
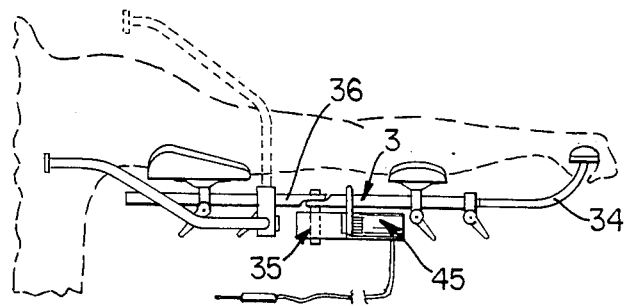
FIG. 8 illustrates a modified arm support, again with a motorized unit for exercising the elbow joint.

FIG. 8 shows an elongated support or rail 3 which also comprises a motorized pivoting unit 45 for the coupling 35 defining an axis which intersects the elbow joint of the arm resting on the support 3. The unit 45 ensures that the portion 34 of the support 3 can pivot with reference to the portion 36 so that the lower arm is pivoted with reference to the upper arm through a desired angle which can be selected in the same way as described with reference to FIGS. 1 and 10. The control unit for the unit 45 of FIG. 8 can be incorporated into the control unit 32 so that the movements of the lower arm can be programmed in advance together with the movements of the entire arm relative to the axis 23 and/or 24. The same applies for the units 33 of FIGS. 2 and 9.

An important advantage of the improved apparatus is that it is substantially portable, i.e., that it can be borne by the patient so that the patient retains her or his mobility while being in a position to exercise the afflicted elbow and/or shoulder joint as often and as long as necessary or tolerable.

Another important advantage of the improved apparatus is that the positions of the various pivot axes with reference to the afflicted joint or joints can be selected and thereupon maintained with a high degree of accuracy and in a rather simple way. Moreover, the adjustments can be carried out by the patient, particularly by an adult or adolescent patient, so that the cost of postoperative treatment involving the exercise of an afflicted elbow and/or shoulder joint can be reduced considerably, not only because the adjustments can be carried out by the patient but also because the patient can be released from a hospital or sanitarium much earlier than if the exercising apparatus were tied to a frame or chair in a hospital or the like.

An additional important advantage of the improved apparatus is that, as a rule, the non-afflicted shoulder can cooperate with the hip region or with the region of the buttocks to bear the carriage and hence the arm support in a manner such that the afflicted joint or joints are relieved of stresses and can heal faster than when the positions of the pivot axes are likely to shift due to the mounting of the carriage on a stationary frame or the like. The placing of a component of the affixing means around or onto the non-afflicted shoulder allows for utilization of the improved apparatus practically immediately after surgery or other treatment of the afflicted joint or joints. Thus, the shoulder pad or strap greatly relieves the afflicted shoulder and allows for an exercising of the afflicted shoulder joint at a much earlier stage of convalescence than when the apparatus is mounted on a stationary frame or the like and only the support is attached to the body (arm) of the patient.

Still another important advantage of the improved apparatus is its ability to allow for adjustment of the positions of various pivot axes within a wide range and with a high or extremely high degee of accuracy, as well as its ability to maintain the pivot axes in selected positions with reference to each other and with reference to the respective joint or joints for any desired interval of time. Moreover, such adjustability of the apparatus renders it possible to attach it to tall, short, chunky, slim, older or youthful patients with the same degree of facility and reliability.

The placing of one of the units 5, 6 at a level above the afflicted shoulder joint and of the other of these units at a level below the afflicted shoulder joint (adjacent to the chest or to the back of the patient) exhibits the advantage that these units do not interfere with movements of the arm and/or a portion of the arm to the extent which is required for adequate exercising and rapid recovery. The units 5 and 6 are simple, compact and capable of being placed close to the respective joints so as to avoid the need for lengthy, bulky, expensive and complex motion transmitting linkages or analogous mechanisms.

An advantage of mounting the unit 6 on the output element of the unit 5 is that the unit 6 shares all movements of such output element and the support 3 can simultaneously perform movements about several mutually inclined axes if such type of exercise is prescribed by a physician or another competent person.

The provision of an affixing device which includes several spaced-apart components contributes to the versatility and convenience of wearing of the improved apparatus. Thus, the upper component including the shoulder pad 10 or strap 40 ensures that the positions of the axes 23, 24 with reference to the shoulder joint S remain at least substantially unchanged whereas the lower component transmits the weight of the apparatus and/or other stresses to the torso of the patient so that at least the major part of the weight is borne by the hips or the region of the body which is adjacent to the hips. The lower component 13, 14 which is shown in FIG. 1 is particularly advantageous if the patient is to be treated in upright position and/or if the patient desires to move around while exercising her or his arm and the afflicted shoulder joint. The lower component which is shown in FIG. 7 is desirable and advantageous when the patient is to remain in seated position and also when an even greater percentage of the weight of the apparatus is to be taken up by the lower component. Moreover, such construction of the lower component enables the patient to sway and/or otherwise move her or his torso with reference to the lower extremities.

The improved apparatus reduces the likelihood of discomfort to the patient, even if one or more afflicted joints are exercised shortly after surgery or during any stage of an illness which necessitates such exercises. The result is that the apparatus reduces the likelihood of the development of stiff joints, more rapidly restores full or partial mobility of the joint or joints and/or shortens the duration of illness or recovery. The arm containing the afflicted elbow joint or being attached to the torso by the afflicted shoulder joint need not be heavily bandaged (which would reduce the mobility of the arm and would cause discomfort due to heat and/or pressure) or need not be bandaged at all. Moreover, the apparatus can be put to use whenever desired so that the patient can be caused or induced to exercise at regular or desired intervals at any time of the day or night. The exercises can be performed for shorter or longer intervals, at a constant or variable speed, and they can be carried out while the patient is alone, i.e., without the need for attendance by skilled and highly salaried persons.

For example, the apparatus can be put to use already two or three days following surgery involving stitching together or plastic coating of ruptures of a rotator as long as the stitches are not subjected to tensional stresses. To this end, the surgeon will normally examine the tension of stitches and will make an appropriate entry in her or his report so that the entry can be considered when a decision is to be rendered as to the timing of the first exercise or exercises as well as the extent and duration of the exercises. Furthermore, the support 3 can be applied and the apparatus put to use two or three days following removal of calciferous deposits from the joint or joints.

The improved apparatus also allows for composite movements of the arm, e.g., for rotatory movements. The extent of such movements will depend on the nature of illness or surgery and on the extent of discomfort which certain stages of rotatory movement are likely to cause to a patient, especially shortly after a surgery or during a particular stage of an illness. The apparatus can be put to use shortly after implantation of shoulder end prostheses as well as following practically all kinds of osteosynthesis. Other situations which render the use of the improved apparatus advisable and beneficial include immobilization of shoulders during narcosis, shoulder contusions and tears, all kinds of illnesses which entail the danger of stiffening of joints, after surgery in the region of the elbow, lower arm or upper arm of a patient including osteosynthesis, arthrolysis, arthrotomy, tenotomy and denervation in the event of epicondylitis, surgery to replace tendons, neurolysis and others. Still further, the apparatus can be used with advantage by patients during recovery from a wide variety of illnesses which need not necessarily be cured by surgery but require extensive or less intensive exercise in order to avoid contraction. The patient can terminate the exercise as soon as it causes excessive discomfort or other undesirable consequences such as signs of infection, swelling and/or others.

The weight of the entire apparatus need not exceed four kilograms especially if the motor 42b and the parts receiving motion therefrom are omitted. The apparatus can be furnished with two supports, one for each arm of a patient. All parts which directly contact the body of the patient can be coated with foam rubber or a like material, or they can be provided with cushions of soft material to reduce the likelihood of discomfort to the patient. The positions of the cushions 37 can be adjusted and such cushions can be releasably held in selected positions by clamping devices or the like (see FIGS. 6 and 7). The connections between the cushions 37 and the main portion of the support 3 can include universal joints (such as the joint 11a') in order to ensure practically universal adjustability of such cushions for greater comfort to the patient. The number of cushions can be reduced to two or increased to four or more.

The utilization of energy from an outlet (see the plugs of the control units 32 shown in FIGS. 6 and 7) is desirable and advantageous because the patient need not carry the battery or batteries 232. On the other hand, the utilization of a battery is desirable when the patient does not wish to be restricted to movements not far away from an outlet. The weight of the battery 232 which is shown in FIGS. 6 and 7 need not exceed 2¼ kilograms. Such battery can be used for a total of up to or even in excess of four hours of exercise without recharging.

The extent of movement of the support 3 can be selected within any desired practical range. For example, the patient can cause the support 3 to pivot about the axis 24 through an angle of up to 90 degrees and through an angle of 80 degrees about the axis 23 (60 degrees forwardly and 20 degrees rearwardly from the standard or normal position shown in FIG. 1). Rotatory movements can involve turning through 60 degrees forwardly and through the same angle in the rearward direction. As a rule, the velocity of movement about the axis 23 and/or 24 is constant during actual exercising but the velocity is preferably adjustable within any desired range as long as it is not excessive for the comfort and health of the patient. The prime mover 19 of the unit 33 or 45 preferably receives energy from the same source as the prime movers 19 of the units 5 and 6. For example, the unit 33 or 45 can be constructed and assembled in such a way that the portion 34 of the support 3 can pivot with reference to the portion 36 through an angle of up to 130 degrees.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of our contribution to the art and, therefore, such adaptations should and are intended to be comprehended within the meaning and range of equivalence of the appended claims.

We claim:

1. Portable apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separably affixing the carriage to the body of the patient; and means for articulately connecting the carriage to said support so as to define two pivot axes which intersect the afflicted shoulder joint, comprising first self-locking transmission means defining one of said pivot axes, means for pivoting said support about said one axis, and second self-locking transmission means defining the other of said axes.

2. The apparatus of claim 1, further comprising means for pivoting said support about said second axis.

3. The apparatus of claim 2, wherein one of said axes is substantially vertical when the patient wearing the apparatus maintains his or her torso in a substantially upright position.

4. The apparatus of claim 2, wherein one of said axes is substantially horizontal when the patient wearing the apparatus maintains his or her torso in a substantially upright position.

5. The apparatus of claim 2, wherein said carriage includes a supporting member for one of said transmission means, the transmission means receiving motion from said one pivoting means having an output element and the other of said transmission means being mounted on said output element.

6. Apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separably affixing the carriage to the body of the patient; and means for articulately connecting the carriage to said support so as to define at least one pivot axis which intersects the afflicted shoulder joint, including first self-locking transmission means defining said one axis and being located at a level above the afflicted shoulder joint of the patient wearing the apparatus when the patient maintains the torso in a substantially upright position, second self-locking transmission means defining for said support a second pivot axis which intersects said one axis close to or in the afflicted shoulder joint of the patient wearing the apparatus, said second transmission means being located at a level below the afflicted shoulder joint when the patient maintains the torso in a substantially upright position, said one axis being substantially vertical and said second axis being substantially horizontal in the upright position of the patient's torso.

7. The apparatus of claim 6, wherein said second transmission means is adjacent to the chest of the patient wearing the apparatus.

8. The apparatus of claim 6, wherein said second transmission means is adjacent to the back of the patient wearing the apparatus.

9. Apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separably affixing the carriage to the body of the patient; and means for articulately connecting the carriage to said support so as to define at least one pivot axis which intersects the afflicted shoulder joint, comprising first self-locking transmission means defining said one pivot axis, self-locking transmission means defining for said support a second pivot axis which intersects said one pivot axis close to or in the afflicted shoulder joint of the patient wearing the apparatus, first and second prime mover means for respectively pivoting said support about said one axis and said second axis, and control means for operating said prime mover means.

10. The apparatus of claim 9, wherein said control means includes means for operating said prime mover means in accordance with a predetermined program.

11. The apparatus of claim 9, further comprising means for monitoring the extent and/or direction of movements of said support about said axes and for transmitting to said control means signals denoting the extent and/or direction of movement of said support about said axes.

12. The apparatus of claim 9, further comprising friction clutch means interposed between said support and at least one of said transmission means so as to permit for operation of the respective prime mover means while said support assumes at least one end position as considered in the direction of pivotal movement of said support about the respective axis.

13. Portable apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separably affixing the carriage to the body of the patient; and means for articulately connecting the carriage to said support so as to define at least one pivot axis which intersects the afflicted shoulder joint, comprising transmission means defining said one pivot axis and means for pivoting said support about said one axis, said transmission means including a self-locking transmission having an input element and an output element transmitting motion to said support, said pivoting means comprising prime moving means for said input element, wherein said connecting means further comprises second transmission means defining a second pivot axis which intersects said one pivot axis at least close to the afflicted shoulder joint of the patient wearing the apparatus and means for pivoting said support about said second axis, said transmission means including a second self-locking transmission having an input element and an output element transmitting motion to said support, said means for pivoting the support about said second axis including prime mover means for the input element of said second self-locking transmission.

14. Apparatus for exercising an afflicted elbow and/or shoulder joint of patient, particularly for postoparative exercising of such joint or joints, comprising an elonagted support for that arm which is attached to the torso of the patient by the afflicted shoulder joint and/or includes the afflicted elbow joint; a carriage for the support; means for separably affixing the carriage to the body of the patient; and means for articulately connecting the carriage to said support so as to define at least one pivot axis which intersects the afflicted shoulder joint, including first self-locking transmission means defining said one axis, second self-locking transmission means defining a second pivot axis intersecting said one axis in or close to the afflicted shoulder joint of the patient wearing the apparatus, and means for adjusting the position of at least one of said transmission means relative to the other transmission means and hence with reference to the afflicted shoulder joint of the patient wering the apparatus.

15. Apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separably affixing the carriage to the body of the patient; and means for articulatly connecting the carriage to said support so as to define at least one pivot axis which intersects the afflicted shoulder joint, including a first unit having means for pivoting said support about said one axis and said one axis being substantially horizontal when the patient wearing the apparatus maintains the torso in a substantially upright position, said unit further having an arcuate bracket overlying the afflicted shoulder and said connecting means further including a second unit having means for pivoting said support with reference to said bracket about a second axis which is substantially vertical when the patient maintains the torso in a substantially upright position, said bracket including a first end portion which is turnable about said one axis and a second end portion which is turnable about said second axis and is substantially normal to said first portion.

16. Apparatus for exercising an afflicted elbow and/or shoulder joint of a patient, particularly for postoperative exercising of such joint or joints, comprising an elongated support for that arm which is attached to the torso of the patient by the afflicted shoulder joint and/or includes the afflicted elbow joint; a carriage for the support; means for separable affixing the carriage to the body of the patient; and means for articulately connecting the carriage to said support so as to define at least one pivot axis which intersects the afflicted shoulder joint, comprising self-locking transmission means defining said one axis and means for pivoting said support about said one axis, said carriage comprising holder means which is connected to said connecting means, said holder means and said pivoting means being adjustable with reference to each other about a further axis which is substantially normal to said one axis.

* * * * *